United States Patent
Matsushima et al.

(10) Patent No.: US 6,903,146 B2
(45) Date of Patent: Jun. 7, 2005

(54) PROSTHETIC FILLER FOR A LIVING BODY AND METHOD OF MANUFACTURING THE PROSTHETIC FILLER

(75) Inventors: Asako Matsushima, Saitama (JP); Masanori Nakasu, Tokyo (JP); Takahiro Fukuhara, Ibaraki (JP)

(73) Assignees: PENTAX Corporation, Tokyo (JP); Katakura Chikkarin Co., Ltd., Tokyo (JP)

( * ) Notice: Subject to any disclaimer, the term of this patent is extended or adjusted under 35 U.S.C. 154(b) by 450 days.

(21) Appl. No.: 10/134,588

(22) Filed: Apr. 30, 2002

(65) Prior Publication Data

US 2002/0169506 A1 Nov. 14, 2002

(30) Foreign Application Priority Data

May 2, 2001 (JP) .................................... 2001-135131

(51) Int. Cl.[7] .............................. A61F 2/02; A61K 9/14; C08J 9/32; C08K 3/32
(52) U.S. Cl. ..................... 523/113; 523/218; 524/415; 424/489; 424/493
(58) Field of Search ............................ 523/113, 218; 524/415; 424/489, 493

(56) References Cited

U.S. PATENT DOCUMENTS

| | | |
|---|---|---|
| 5,064,436 A | 11/1991 | Ogiso et al. |
| 5,082,803 A | 1/1992 | Sumita |
| 5,180,426 A | 1/1993 | Sumita |
| RE35,267 E * | 6/1996 | Tsuru et al. ................. 210/692 |
| 5,540,995 A | 7/1996 | Kitano et al. |
| 5,679,723 A * | 10/1997 | Cooper et al. .............. 523/115 |
| 5,851,670 A * | 12/1998 | Mitoh et al. ................. 428/403 |
| 5,866,155 A | 2/1999 | Laurencin et al. |
| 5,897,953 A | 4/1999 | Ogawa et al. |
| 6,187,046 B1 | 2/2001 | Yamamoto et al. |
| 6,203,574 B1 | 3/2001 | Kawamura |

FOREIGN PATENT DOCUMENTS

| | | |
|---|---|---|
| EP | 0416398 | 3/1991 |
| GB | 2031450 | 4/1980 |
| JP | 3-162863 | 7/1991 |
| JP | 8-182753 | 7/1996 |
| JP | 11128336 | 5/1999 |
| JP | 2984112 | 9/1999 |
| JP | 11244373 | 9/1999 |
| JP | 11276510 | 10/1999 |
| JP | 2000-189510 | 7/2000 |

OTHER PUBLICATIONS

English Language Abstract of JP 8–182753.
English Language Abstract of JP 11–128336.
English Language Abstract of JP 11–244373.
English Language Abstract of JP 11–276510.
English Language Abstract of JP 2000–189510.

* cited by examiner

Primary Examiner—Tae H. Yoon
(74) Attorney, Agent, or Firm—Greenblum & Bernstein P.L.C.

(57) ABSTRACT

A prosthetic filler for a living body having excellent storage properties and handlability is disclosed. The prosthetic filler includes calcium phosphate granules and porous small chips made of an organic material for binding these calcium phosphate granules to each other. The prosthetic filler is made by mixing the calcium phosphate granules and the small chips of the organic material. When the prosthetic filler is used for a living body, it is added with water, and then they are kneaded to become a paste state. Thus obtained paste state prosthetic filler is injected into a bone defect site or the like to restore it.

20 Claims, No Drawings

PROSTHETIC FILLER FOR A LIVING BODY AND METHOD OF MANUFACTURING THE PROSTHETIC FILLER

BACKGROUND OF THE INVENTION

1. Field of the Invention

This invention relates to a prosthetic filler for a living body (hereinafter, simply referred to as "prosthetic filler") which is mainly used for medical and dental purposes, and a method of manufacturing the prosthetic filler.

2. Description of the Prior Art

In medical and dental fields, calcium phosphate is used as a material for artificial bones and bone prostheses. For example, when a defect is produced in a bone due to bone fracture, bone tumor or the like, the bone defect site is restored or repaired by using a bone prosthesis made of calcium phosphate.

As for such a bone prosthesis made of calcium phosphate, a bone prosthesis of block type and a bone prosthesis of granule type are known. Examples of the block type bone prosthesis are disclosed in Japanese Patent Laid-open No. Hei 8-182753, Japanese Patent Laid-open No. Hei 11-128336, Japanese Patent Laid-open No. Hei 11-244373, Japanese Patent Laid-open No. Hei 11-276510, and Japanese Patent Laid-open No. 2000-189510, and the like.

However, the block type bone prosthesis needs to be formed into a shape of a bone defect site by using a handpiece or the like at an operation site, and thus use of the block type bone prosthesis involves troublesomeness.

Further, it is difficult to use the block type bone prosthesis in a case where the shape of the bone defect site is complicated or in a case where the operation must be performed quickly. In addition to this, the block type bone prosthesis is not suitable for restoring a defect of soft tissue.

On the other hand, since the granule type bone prosthesis has flexibility in shape due to its granular form, it is possible to restore a bone defect site only by pouring it into the site. For this reason, use of such a granule type bone prosthesis makes it possible to perform an operation smoothly and speedily.

However, when the bone prosthesis is constituted from calcium phosphate granules only, there is a drawback that such a bone prosthesis is difficult to handle or use at the operation site, that is handlability thereof at the operation site is lowered. For example, there is a case that when the granule type bone prosthesis is to be filled into a bone defect site, a part of the granules is spilled and it is dissipated to irrelevant portions other than the bone defect site. Also, there is a case that a part of the granules filled in the bone defect site will be dissipated out of the bone defect site after the operation.

In order to solve these problems, a bone prosthesis having improved handlability at the operation site has been developed, which is disclosed in Japanese Patent Laid-open No.Hei 3-162863, for example. In this bone prosthesis, calcium phosphate granules are kneaded with polymeric material in order to improve handlability thereof. However, this bone prosthesis has a problem in that it is liable to be deteriorated, and thus it is not suitable for storage for a long period of time.

SUMMARY OF THE INVENTION

It is therefore an object of the present invention to provide a prosthetic filler for a living body having excellent storage properties and handlability, and a method of manufacturing such a prosthetic filler.

In order to achieve the object mentioned above, the present invention is directed to a prosthetic filler for a living body, which comprises calcium phosphate granules and porous small chips made of an organic material for binding the calcium phosphate granules. This makes it possible to obtain a prosthetic filler for a living body which is suitable for storage and easy to handle.

In the present invention described above, it is preferred that the calcium phosphate granules and the small chips are mixed with each other to make the prosthetic filler. The prosthetic filler comprised of such a mixture is easy to use.

Further, it is also preferred that the bulk density of the small chips is in the range of 0.01 to 1 $g/cm^3$. This makes it possible to prevent deterioration of the organic material constituting the small chips while maintaining solubility of the small chips to water.

Furthermore, it is also preferred that the average volume per one small chip is in the range of 0.001 to 500 $mm^3$. This makes it possible to more effectively enjoy the effects described above.

Moreover, it is also preferred that the small chips are formed from a solution containing the organic material. By forming a solid substance of the organic material from the organic material solution, it becomes possible to prepare porous small chips with ease.

In this case, it is also preferred that the small chips are formed by freeze-drying the solution containing the organic material. According to this method, particularly excellent porous small chips can be made.

In the present invention, it is preferred that the organic material is made of polysaccharides. By using polysaccharides as the organic material, the prosthetic filler can have excellent biocompatibility and shaping properties when it is in a paste state.

In this case, it is preferred that the organic material is made of non-human origin polysaccharides. This reduces the risk of causing infectious diseases. Preferably, the organic material is chitins, since chitins have an excellent property that induces osteoblast to activate the regeneration of bone.

In the present invention, it is preferred that the calcium phosphate is hydroxyapatite. This is because hydroxyapatite has an excellent property that dose not cause rejection reaction in a living body.

Further, it is preferred that the mass ratio of the calcium phosphate granules and the small chips is in the range of 1:0.5 to 1:10. This makes it easier to restore a bone defect site with the prosthetic filler. Further, such a prosthetic filler dose not cause rejection reaction in a living body after it is filled in the bone defect site so that it can be directly bonded to autologous bone.

Furthermore, it is also preferred that the bulk density of the prosthetic filler is in the range of 0.01 to 1 $g/cm^3$. This improves solubility of the prosthetic filler in water.

Moreover, in the present invention, it is also preferred that the prosthetic filler becomes a paste state when water is added thereto and then it is kneaded. This paste state prosthetic filler is especially appropriate for restoring a born defect site.

In this case, it is preferred that the paste state prosthetic filler is used by being charged into an injection instrument. According to this, it becomes extremely easy to restore a bone defect site with the prosthetic filler.

Another aspect of the present invention is directed to a method of manufacturing a prosthetic filler for a living body. The method comprises the steps of preparing porous small chips made of an organic material for binding calcium phosphate granules, and mixing the small chips with calcium phosphate granules. This makes it possible to obtain a prosthetic filler having excellent storage properties and handlability.

In this method, it is preferred that the small chips are formed through a step of solidifying an organic material solution in which the organic material is dissolved. By forming a solid substance of the organic material from the organic material solution, it is possible to easily prepare the porous small chips.

Further, in this case, it is also preferred that the small chips are formed through a step of freeze-drying the solution in which the organic material is dissolved. According to this method, it is possible to easily obtain a porous organic material from the organic material solution without change and deterioration of its properties.

Furthermore, in the above method, it is also preferred that the concentration of the organic material in the solution is in the range of 0.1 to 20 wt %. This makes it possible to obtain porous small chips of the organic material having appropriate pores, and such porous small chips can be easily dissolved in water and are suitable for storage.

Moreover, it is also preferred that the small chips are formed by breaking the solidified organic material into small chips. This method is extremely suitable for forming the small chips.

In the above method, it is also preferred that the porosity of each of the small chips is in the range of 50 to 99%.

Moreover, it is also preferred that water is added to the mixture of the small chips and the calcium phosphate granules, and then it is kneaded to be in a paste state. This paste state prosthetic filler is appropriate for restoring a bone defect site.

DETAILED DESCRIPTION OF THE INVENTION

Hereinbelow, a preferred embodiment of a prosthetic filler for a living body (hereinafter, simply referred to as "prosthetic filler") according to the present invention and a method of manufacturing the prosthetic filler will be described in detail.

The following description will be made with regard to the case where the prosthetic filler according to the present invention is used as a bone prosthesis. In this regard, however, it is to be noted that the term "bone" used in this specification has a broad meaning that includes not only bone but also teeth.

The prosthetic filler of the present invention includes calcium phosphate granules and porous small chips made of an organic material having a function of binding the calcium phosphate granules. The calcium phosphate granules and the porous small chips of the organic material are mixed with each other. That is, the prosthetic filler of the present invention is in the form of powder, and thus various shapes of containers can be used for storing the prosthetic filler.

The prosthetic filler is being stored in a dried state. When the prosthetic filler is used for a living body, it is added with water, and then they are kneaded. By doing so, the small chips contained in the prosthetic filler are dissolved so that the prosthetic filler becomes a paste state. Thus obtained paste state prosthetic filler is injected and filled into a bone defect site or the like by using an injection instrument such as a syringe or the like.

As described above, since the prosthetic filler of the present invention is capable of being filled into the bone defect site by such a simple operation, the prosthetic filler of the present invention is excellent in handlability. Further, the prosthetic filler of the present invention is hard to be deteriorated. Therefore, the prosthetic filler of the present invention is suitable for storage for a long period of time.

Hereinbelow, respective components of the prosthetic filler of the present invention will be described.
<Calcium Phosphate Granules>

In the present invention, the calcium phosphate granules mean grains or powder of calcium phosphate, for example.

The calcium phosphate (calcium phosphate based compound) to be used for the prosthetic filler of the present invention is not limited to a specific one, but it is preferable to use calcium phosphate having Ca/P ratio of 1.0 to 2.0.

Examples of such calcium phosphate include apatites such as hydroxyapatite, fluorapatite, carbonate apatite; calcium hydrogen phosphate (anhydride or dehydrate thereof); tricalcium phosphate; tetracalcium phosphate; octacalcium phosphate; and the like. These calcium phosphates may be used alone or as a combination of two or more of them.

Among these calcium phosphates, hydroxyapatite is preferably used as the calcium phosphate in the present invention, because hydroxyapatite is particularly excellent in that it dose not cause rejection reaction in a living body.

In this regard, it is to be noted that the average grain size of the calcium phosphate granules is not limited to a specific value, but it is preferably in the range of about 10 to 6,000 $\mu$m, and more preferably in the range of about 40 to 4,000 $\mu$m. By setting the value of the average grain size to the above range, it becomes easy to handle the prosthetic filler, that is handlability of the prosthetic filler is improved.

Further, as for the grain size distribution of the calcium phosphate granules, it is preferred that the grain sizes of at least 60% of all the calcium phosphate granules are included in the range of ±250 $\mu$m of the average grain size, and more preferably in the range of ±200 $\mu$m of the average grain size. If the grain size distribution is within the above range, the handlability of the prosthetic filler is further improved.

Furthermore, such calcium phosphate granules described above are preferably subjected to burning. By doing so, it is possible to easily prevent impurities, foreign substances, and the like from being contained in the calcium phosphate granules. In this regard, it is to be noted that the burning condition may be in the range of 700 to 1,550° C. for 0.5 to 24 hours under an atmospheric pressure or a reduced pressure, for example.
<Small Chips of Organic Material>

The organic material (binder) has a function of binding the calcium phosphate granules to each other when water is added to the mixture of the calcium phosphate granules and the organic material. In addition, this organic material also has a function of adjusting the viscosity of the prosthetic filler when water is added thereto, thereby giving shaping properties and shape-retaining properties to the prosthetic filler.

In the present invention, this organic material is formed into porous small chips (flakes or small pieces). This makes it possible to give excellent storage properties and handlability to the prosthetic filler.

In this regard, it is to be noted that normally organic materials such as carboxymethyl chitin or the like have a characteristic that, when they are dissolved in water, their viscosity will decrease with a lapse of time similarly to typical polysaccharides. However, as described above, the prosthetic filler of the present invention is stored in a dried state until it is used, that is, the organic material contained in the prosthetic filler is solidified. Therefore, according to the prosthetic filler of the present invention, it is possible to preferably prevent the organic material from being changed in quality and deteriorated.

Further, when the prosthetic filler of the present invention is added with water, the organic material contained therein is readily dissolved in a short period of time. This results from that the organic material is formed into porous small chips. Specifically, in the prosthetic filler of the present invention, pores of the small chips of the organic material appropriately increase the contact area between the organic material and the water. Further, water can readily permeate into the chips due to their small sizes. For these reasons, the organic material of the prosthetic filler of the present invention can be easily dissolved in water.

In addition, since the prosthetic filler of the present invention is in the form of powder as described above, the prosthetic filler can be easily stirred when water is added thereto.

Consequently, the prosthetic filler of the present invention can easily and speedily become a paste state when it is used at the operation site. Thus obtained paste state prosthetic filler can be easily used to restore a bone defect site only by injecting it into the bone defect site. Further, since such a prosthetic filler has some fluidity with appropriate viscosity, the prosthetic filler is filled into the bone defect site so that it reliably follows the shape of the bone defect site. Therefore, the prosthetic filler of the present invention can be used for bone defect sites having various shapes.

As described above, in the present invention, the organic material is formed into porous small chips (flakes), whereby both the storage properties and the handlability of the prosthetic filler are satisfactorily attained.

In order to obtain the effects described above more effectively, it is preferred that the small chips of the organic material satisfy at least one of the following conditions.

The bulk density of the small chips is preferably in the range of about 0.01 to 1 $g/cm^3$, and more preferably in the range of about 0.02 to 0.1 $g/cm^3$. The inventors of the present invention have found that the bulk density of the small chips is extremely important in attaining both the storage properties of the organic material and the solubility of the organic material. Additionally, the inventors have also found that by setting the bulk density of the small chips to the above range, both the storage properties of the organic material and the solubility of the organic material in water can be extremely satisfactorily attained.

Further, the average volume per one small chip is preferably in the range of about 0.001 to 500 $mm^3$, and more preferably in the range of about 0.1 to 100 $mm^3$. If the volume per one small chip exceeds the above upper limit value, there is a case that the solubility of the organic material in water is lowered. On the other hand, if the volume per one small chip is lower than the above lower limit value, there is a case that the organic material is liable to be deteriorated during its storage.

From the same view point as described above, the average surface area of the outer surface per one small chip is preferably in the range of about 0.05 to 300 $mm^2$, and more preferably in the range of about 1 to 100 $mm^2$.

As for the last condition, the average value of the outer surface area/volume per one small chip is preferably in the range of about 0.6 to 50 $mm^2/mm^3$, and more preferably in the range of about 1 to 10 $mm^2/mm^3$. By setting the average value of the outer surface area/volume per one small chip to the above range, it becomes possible to obtain such effects as described above more effectively.

Hereinbelow, a description will be made with regard to the organic material constituting the small chips.

Examples of the organic material include monosaccharides such as glucose, fructose; oligosaccharides such as saccharose, maltose, lactose; polysaccharides such as carboxymethyl chitin, carboxymethyl cellulose, starch, glycogen, pectin, chitin, chitosan; water-soluble (or hydrophilic) polymeric materials such as glycerin, sugar alcohol (e.g., sorbitol, mannitol, xylitol), gelatin, polyvinyl alcohol, maleic anhydride; and the like.

Among these organic materials, polysaccharides are particularly preferred as the organic material, because polysaccharides have excellent shaping properties and biocompatibility. Further, among these polysaccharides, polysaccharides of non-human origin such as carboxymethyl chitin, carboxymethyl cellulose, starch, pectin, chitin, chitosan, and the like are preferably used as the organic material. In such non-human origin organic materials, raw materials thereof are derived from sources other than human beings. By using the non-human origin organic material as the organic material, the risk of causing infectious diseases is decreased. In addition, since the degradation speed in a living body of the non-human origin organic material is not too fast or too slow, the prosthetic filler containing such organic material is suitable for regeneration of bone. In this regard, it is to be noted that non-human origin material is generally characterized in that raw materials thereof are derived from sources other than human beings.

Among these non-human origin polysaccharides, chitins such as chitin and chitin derivatives (e.g., chitosan, carboxymethyl chitin, and the like) are particularly preferred as the organic material, because chitins have an excellent property that induces osteoblast to activate the regeneration of bone.

In this regard, it is to be noted that the small chips may contain substances (additives) other than such organic materials described above.

The prosthetic filler described above may contain a pH regulator, an antimicrobial agent, an X-ray contrast medium, other various chemicals, and the like.

<Manufacture of Prosthetic Filler>

Hereinbelow, a description will be made with regard to an embodiment of a method of manufacturing the prosthetic filler.

<1> First, an organic material is dissolved in water (solvent) to prepare an organic material solution.

The concentration of the organic material in the organic material solution is preferably in the range of about 0.1 to 20 wt %, and more preferably in the range of about 0.5 to 12 wt %. By setting the concentration of the organic material to the above range, a porous substance of the organic material which will be obtained in the following step can have appropriate pores, and the porous substance having such pores can be easily dissolved in water and is suitable for storage.

Further, the viscosity of the organic material solution is not limited to a specific value, but it is preferably in the range of about 100 to 100,000 cps, and more preferably in the range of about 500 to 10,000 cps at a room temperature (e.g., 25° C.). By setting the viscosity of the organic material to the above range, a prosthetic filler for a living body to be obtained can have an improved handlability.

Furthermore, the pH of the organic material solution is not limited to a specific value, but it is preferably in the range of about 3 to 10, and more preferably in the range of about 4 to 8.

<2> Next, the organic material in the organic material solution is solidified to obtain a porous substance of the organic material.

The porosity of the porous substance is not limited to a specific value, but it is preferably in the range of about 50 to 99%.

Examples of a method of solidifying the organic material include a freeze-drying method, vacuum-drying method, heat-drying method, and the like. Among these methods, a freeze-drying method is preferred. According to the freeze-drying method, the organic material is not liable to be changed in quality and deteriorated.

In a case where the organic material is solidified by the freeze-drying method, the freezing temperature of the organic material solution is not limited to a specific value, but it is preferably in the range of about −90 to −10° C. The drying pressure is not also limited to a specific value, but it is preferably in the range of about 0.004 to 1 mmHg, and more preferably in the range of about 0.004 to 0.2 mmHg. The drying time is not also particularly limited, but it is preferably in the range of about three hours to one week. By respectively setting the freezing temperature, the drying pressure, and the drying time to the above ranges, it is possible to easily form the porous substance of the organic material having appropriate porosity and pore size by which such effects as described above can be obtained more conspicuously. In this regard, it is to be noted that the organic material solution may be subjected to pre-freezing prior to the freeze-drying.

<3> Next, thus obtained porous substance (solidified substance) of the organic material is broken into small chips (or small flakes). In this case, it is preferred that the porous substance of the organic material is broken into small chips so as to satisfy the preferred ranges of the above mentioned conditions.

Such small chips of the organic material can be preferably obtained by grinding or pulverizing the porous substance of the organic material by means of a grinder (pulverizer).

<4> Thereafter, the small chips of the organic material are mixed with the calcium phosphate granules (which are separately prepared). By doing so, the prosthetic filler can be obtained.

In this case, the mixing ratio (mass ratio) of the calcium phosphate granules and the small chips of the organic material is preferably in the range of about 1:0.5 to 1:10, and more preferably in the range of about 1:0.8 to 1:10. That is, the mixing ratio (mass ratio) of the calcium phosphate granules and the small chips of the organic material in the prosthetic filler is preferably in the range of about 1:0.5 to 1:10, and more preferably in the range of about 1:0.8 to 1:10. By setting the mixing ratio to the above range, it becomes easier to fill a bone defect site with the prosthetic filler for restoration thereof, and further the bone will be smoothly regenerated after the restoration.

In this regard, it is to be noted that the mixing ratio of the calcium phosphate granules and the organic material can be arbitrarily varied depending on locations and conditions of use of the prosthetic filler. For example, in a case where the prosthetic filler of the present invention is used for bone defects on which heavy load is exerted, the amount of the calcium phosphate granules to be mixed may be increased. By doing so, the strength of the bone defect site restored by the prosthetic filler is increased. Further, in a case where the prosthetic filler is injected into a bone defect site using a syringe, the amount of the organic material to be contained in the prosthetic filler can be increased. Use of such a prosthetic filler makes it easier to inject the prosthetic filler.

Further, the bulk density of the prosthetic filler is not limited to a specific value, but it is preferably in the range of about 0.01 to 1 $g/cm^3$, and more preferably in the range of about 0.05 to 0.5 $g/cm^3$. By setting the bulk density of the prosthetic filler to the above range, the storage properties and the solubility of the prosthetic filler in water are further improved.

<Restoration of Bone Defect Site>

Since such a prosthetic filler as described above is hard to be deteriorated, it is suitable for storage for a long period of time.

When the prosthetic filler is used, a predetermined amount of water (solution) is added thereto, and then the prosthetic filler and the solution are mixed and kneaded. By doing so, the prosthetic filler becomes a paste state (slurry). As described above, the prosthetic filler of the present invention easily becomes a paste state because the small chips of the organic material are readily dissolved in the solution.

The mixing ratio of the prosthetic filler and the solution is not limited to a specific value, and it may be set in the range of about 1:0.5 to 1:20 at the mass ratio, for example.

Examples of solution (solvent) used for making the paste state prosthetic filler include water, isotonic sodium chloride solution (e.g., various kinds of infusion such as Ringer's solution, physical saline, and the like), body fluid (serum, plasma, blood, and the like), other kinds of chemical solution, and the like.

Preferably, as described above, thus obtained paste state prosthetic filler is injected into bone defect sites using an injection instrument such as a syringe (injector), a needle for a syringe, a catheter, or the like. By using a syringe, for example, the prosthetic filler can be supplied to a bone defect site (or the vicinity thereof) only by setting the tip of the syringe to the bone defect site and then pressing a plunger of the syringe. Further, since the tip of the syringe is narrow, the tip of the syringe can be reached to the bone defect site without the need to create a large incision in a skin and a subcutaneous tissue. Therefore, by using the prosthetic filler of the present invention, the area of the incision to be formed in a skin and a subcutaneous tissue when restoring the bone defect site can be reduced.

Further, the paste state prosthetic filler of the present invention can be discharged from the syringe only by applying an appropriate pressure to the plunger of the syringe. This means that in the syringe filled with the paste state prosthetic filler of the present invention, it is easy to finely control the pressure to be applied to the plunger of the syringe. Therefore, according to the prosthetic filler of the present invention, it becomes easy to finely control the amount of the prosthetic filler to be discharged from the syringe.

As described above, the prosthetic filler of the present invention enables to easily perform an operation for restoring a bone defect site. In addition, the prosthetic filler of the present invention reduces the burden on a patient during the operation.

Although the present invention has been described with reference to the preferred embodiment, the present invention is not limited thereto.

For example, in the present invention, the calcium phosphate granules and the small chips of the organic material may be stored separately from each other until the prosthetic filler is used. In this case, they are mixed with each other when the prosthetic filler is actually used.

Further, the prosthetic filler of the present invention may be injected into a mold and then dried to solidify it. In this case, thus obtained solidified prosthetic filler is then filled into a bone defect site.

Furthermore, the prosthetic filler of the present invention may be filled into a bone defect site by using a spoon, a trowel, or the like.

Moreover, the prosthetic filler of the present invention may be used without adding water thereto.

The embodiment of the present invention has been described with reference to the case where the prosthetic filler is used to restore a bone defect site. However, the prosthetic filler of the present invention may be used to restore soft tissue and the like.

EXAMPLES

1. Preparation of Hydroxyapatite Granules

Slurry of hydroxyapatite (having a Ca/P ratio of 1.67) which had been synthesized by a wet process was subjected to spray drying to obtain hydroxyapatite granules. Further, thus obtained hydroxyapatite granules were then subjected to air-classification so that their average grain size was 250 $\mu$M and their grain size distribution was in the range of 150 to 350 $\mu$m. In this regard, it is to be noted that the grain size distribution means that at least 60% of all the granules must be within a range of the grain size of 150 to 350 $\mu$m. (Note that, in this specification, the term "grain size distribution" means the same condition described above.)

Thus obtained hydroxyapatite granules were burned at 1,200° C. for one hour under an atmospheric pressure, to finally obtain calcium phosphate granules with an average grain size of about 200 $\mu$m and a grain size distribution in the range of 100 to 300 $\mu$m.

Further, it was confirmed that the burned granules are surely the granules of hydroxyapatite by performing X-ray diffraction using an X-ray diffraction device ("RINT2200VHF" manufactured by Rigaku Corporation).

2. Preparation of Carboxymethyl Chitin Small Chips

First, carboxymethyl chitin was dissolved in distilled water to prepare 2.0 wt % of carboxymethyl chitin solution.

The viscosity of the carboxymethyl chitin solution at 25° C. was 10,000 cps. At this time, the pH of this solution was 7.2.

Next, the carboxymethyl chitin solution was freeze-dried, and as a result, a porous block of the carboxymethyl chitin was obtained. At this time, the porosity of the porous substance was 95%.

Thereafter, thus obtained porous block was ground or pulverized by means of a grinder (pulverizer), to obtain flake-like small chips having a shape such as wood shavings or slice chips of dried bonito.

The bulk density of the obtained carboxymethyl chitin small chips was 0.05 g/cm$^3$. The average volume per one carboxymethyl chitin chip was 5 mm$^3$.

3. Mixing of Hydroxyapatite Granules and Carboxymethyl Chitin Small Chips

Thus obtained hydroxyapatite granules and the carboxymethyl chitin small chips in such a manner described above were mixed so that the mixing ratio (mass ratio) of them was 1:1.5, thereby obtaining the prosthetic filler of the present invention.

Physical saline was added to the obtained prosthetic filler so that the mass ratio of the prosthetic filler and the physical saline was 1:1.4. Subsequently, this mixture was kneaded by using a rod to become a paste state.

Thereafter, the paste state prosthetic filler of the present invention was filled into a cavity formed in a parietal bone of a rabbit. This operation was performed in such a manner that the prosthetic filler was injected into the cavity formed in the parietal bone of the rabbit using a syringe.

The used prosthetic filler had a just suitable viscosity to be discharged from the syringe by applying pressure to a plunger of the syringe. In addition to this, the prosthetic filler discharged from the syringe also had excellent shaping properties and shape-retaining properties.

After four weeks have passed since the operation, the rabbit was slaughtered, and then the operated site thereof was extracted together with its peripheral tissues from the rabbit, and it was fixed with formaline. Next, the fixed operated site and its peripheral tissues was subjected to decalcification, embedding in resin, and staining, to prepare a specimen.

Observing this specimen by a microscope, it was confirmed that new bone was actively generated after the operation at a site which had been restored by the prosthetic filler.

As has been described above, according to the present invention, it is possible to provide a prosthetic filler having excellent storage properties and handlability.

Since the prosthetic filler of the present invention has such advantages, the prosthetic filler is extremely useful and helpful for medical professionals such as doctors, and the like. Further, the prosthetic filler of the present invention can give patients benefits such as a relief of burden during operation.

Finally, it is to be understood that many changes and additions may be made to the embodiments described above without departing from the scope and spirit of the invention as defined in the following claims.

Further, it is also to be understood that the present disclosure relates to subject matter contained in Japanese Patent Application No. 2001-135131 (filed on May 2, 2001) which is expressly incorporated herein by reference in its entireties.

What is claimed is:

1. A prosthetic filler for a living body, comprising:
   calcium phosphate granules; and
   porous small chips made of an organic material for binding the calcium phosphate granules;
   wherein the calcium phosphate granules and the small chips are mixed with each other to make the prosthetic filler.

2. The prosthetic filler for a living body as claimed in claim 1, wherein the bulk density of the small chips is in the range of 0.01 to 1 g/cm$^3$.

3. The prosthetic filler for a living body as claimed in claim 1, wherein the average volume per one small chip is in the range of 0.001 to 500 mm$^3$.

4. The prosthetic filler for a living body as claimed in claim 1, wherein the small chips are formed from a solution containing the organic material.

5. The prosthetic filler for a living body as claimed in claim 4, wherein the small chips are formed by freeze-drying the solution containing the organic material.

6. A prosthetic filler for a living body, comprising:
   calcium phosphate granules; and
   porous small chips made of an organic material for binding the calcium phosphate granules;
   wherein the organic material is made of polysaccharides.

7. The prosthetic filler for a living body as claimed in claim 6, wherein the organic material is made of non-human origin polysaccharides.

8. The prosthetic filler for a living body as claimed in claim 7, wherein the organic material is chitins.

9. The prosthetic filler for a living body as claimed in claim 1, wherein the calcium phosphate is hydroxyapatite.

10. The prosthetic filler for a living body as claimed in claim 1, wherein the mass ratio of the calcium phosphate granules and the small chips is in the range of 1:0.5 to 1:10.

11. The prosthetic filler for a living body as claimed in claim 1, wherein the bulk density of the prosthetic filler is in the range of 0.01 to 1 g/cm$^3$.

12. A prosthetic filler for a living body, comprising:

calcium phosphate granules; and porous small chips made of an organic material for binding the calcium phosphate granules;

wherein the prosthetic filler becomes a paste state when water is added thereto and then it is kneaded.

13. The prosthetic filler for a living body as claimed in claim 12, wherein the paste state prosthetic filler is used by being charged into an injection instrument.

14. A method of manufacturing a prosthetic filler for a living body, the method comprising:

preparing porous small chips made of an organic material for binding calcium phosphate granules; and mixing the small chips with calcium phosphate granules.

15. The method as claimed in claim 14, wherein the small chips are formed through solidifying an organic material solution in which the organic material is dissolved.

16. The method as claimed in claim 15, wherein the small chips are formed through freeze-drying the solution in which the organic material is dissolved.

17. The method as claimed in claim 16, wherein the concentration of the organic material in the solution is in the range of 0.1 to 20 wt %.

18. The method as claimed in claim 15, wherein the small chips are formed by breaking the solidified organic material into small chips.

19. The method as claimed in claim 18, wherein the porosity of each of the small chips is in the range of 50 to 99%.

20. The method as claimed in claim 14, wherein water is added to the mixture of the small chips and the calcium phosphate granules, and then it is kneaded to be in a paste state.

\* \* \* \* \*